United States Patent
Al-Shehri

(10) Patent No.: US 9,393,089 B1
(45) Date of Patent: Jul. 19, 2016

(54) STABILIZING DEVICE FOR DENTAL CROWNS

(71) Applicant: KING SAUD UNIVERSITY, Riyadh (SA)

(72) Inventor: Huda Ahmed Al-Shehri, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 14/922,104

(22) Filed: Oct. 23, 2015

(51) Int. Cl.
| | |
|---|---|
| *A61C 19/04* | (2006.01) |
| *A61C 5/08* | (2006.01) |
| *F16M 11/04* | (2006.01) |
| *F16B 2/06* | (2006.01) |
| *G01B 11/14* | (2006.01) |

(52) U.S. Cl.
CPC . *A61C 19/04* (2013.01); *A61C 5/08* (2013.01); *F16B 2/065* (2013.01); *F16M 11/041* (2013.01); *G01B 11/14* (2013.01)

(58) Field of Classification Search
CPC ............ B25B 5/101; B25B 5/082; B25B 5/15
See application file for complete search history.

(56) References Cited

U.S. PATENT DOCUMENTS

| | | | | |
|---|---|---|---|---|
| 2,602,358 | A * | 7/1952 | Lile | B21D 1/06 269/143 |
| 2,960,913 | A | 11/1960 | Herrala | |
| 3,342,994 | A | 9/1967 | Franken at al. | |
| 2002/0013532 | A1* | 1/2002 | Czubko | A61B 1/0017 600/478 |
| 2007/0262506 | A1* | 11/2007 | Alberti | B25B 5/067 269/249 |
| 2013/0286174 | A1* | 10/2013 | Urakabe | A61B 1/00009 348/66 |

FOREIGN PATENT DOCUMENTS

| | | |
|---|---|---|
| CN | 202631459 U | 12/2012 |
| DE | 39 16 171 A1 | 11/1990 |

\* cited by examiner

*Primary Examiner* — Lee D Wilson
(74) *Attorney, Agent, or Firm* — Richard C. Litman

(57) ABSTRACT

The stabilizing device for dental crowns includes a U-shaped base, an elongate bottom member extending from the base, and opposing upright members extending from the ends of the bottom member. A clamp assembly is rotatably supported between the upright members. The clamp assembly includes a spindle stock with a holder shaft extending from one of the upright members. The distal end of the holder shaft supports a master model of a patient's tooth. A tail stock with a tail shaft extends from the other upright member. A resilient tip is attached to the distal end of the tail shaft to support a crown thereon. The tail shaft is biased to enable clamping and holding of the crown and master model together via reciprocation of the tail shaft with respect to the holder shaft. Measurement scans may be performed at multiple angular positions through selective rotation of the clamp assembly.

4 Claims, 4 Drawing Sheets

STABILIZING DEVICE FOR DENTAL CROWNS

BACKGROUND OF THE INVENTION

1. Field of the Invention

The present invention relates to dental devices, and particularly to a stabilizing device for dental crowns that permits a user to measure a marginal gap between a crown and a model tooth structure.

2. Description of the Related Art

A dental crown is one of the most common treatments in dentistry. A crown is most effective if it closely resembles tooth structure and does not leave gaps between the edge of the crown and unprepared tooth structure. Any opening or marginal gap in this area will subject the tooth to plaque accumulation which can cause recurrent caries and gum disease.

Many techniques have been described in the literature for measuring the marginal gap. Such techniques include cementing the crowns on stone replicas of prepared teeth and viewing sections with a light microscope. Other techniques include replicating the gap between the crown and the prepared tooth with silicone material and measuring its thickness with light microscopy or computer generated tomography. However, these techniques involve many variables that may cause or lead to errors that ultimately do not reflect the true marginal gap.

A travelling microscope or a measuring microscope is a light microscope that measures linear distances between two points in a horizontal manner within an accuracy of 0.01 inch. It is considered one of the most reliable techniques of measuring marginal gap because it provides direct access to the marginal gap between the crown and a prepared tooth structure. However, there is a need to stabilize the crown/tooth assembly in a repeatable manner under the microscope. Typically, a silicone index is made to stabilize the assembly to enable measurement of one point in one aspect of the assembly. When another point is intended to be measured, a second silicone index is made and so forth. Usually the maximum number that can be achieved is about eight measurements per crown/tooth assembly. It has been reported and suggested that the minimum number of points to measure around the assembly should be fifty so that the mean marginal gap truly represents the actual gap. This is nearly impossible using the silicone index technique.

There is a need for a technique that allows for holding the crown tightly on a prepared tooth structure while allowing for rotation of the crown to measure as many points as required without resorting to numerous silicone indexes.

Thus, a stabilizing device for dental crowns solving the aforementioned problems is desired.

SUMMARY OF THE INVENTION

The stabilizing device for dental crowns includes a U-shaped base with an elongate bottom member and opposing upright members extending from the ends of the bottom member. A clamp assembly is rotatably supported between the upright members. The clamp assembly includes a spindle stock with a holder shaft extending from one of the upright members, The distal end of the holder shaft supports a master model of a patient's tooth. A tail stock with a tail shaft extends from the other upright member. A resilient tip is attached to the distal end of the tail shaft to support a crown thereon. The tail shaft is biased to enable clamping and holding of the crown and master model together via reciprocation of the tail shaft with respect to the holder shaft. Measurement scans may be performed at multiple angular positions through selective rotation of the clamp assembly.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
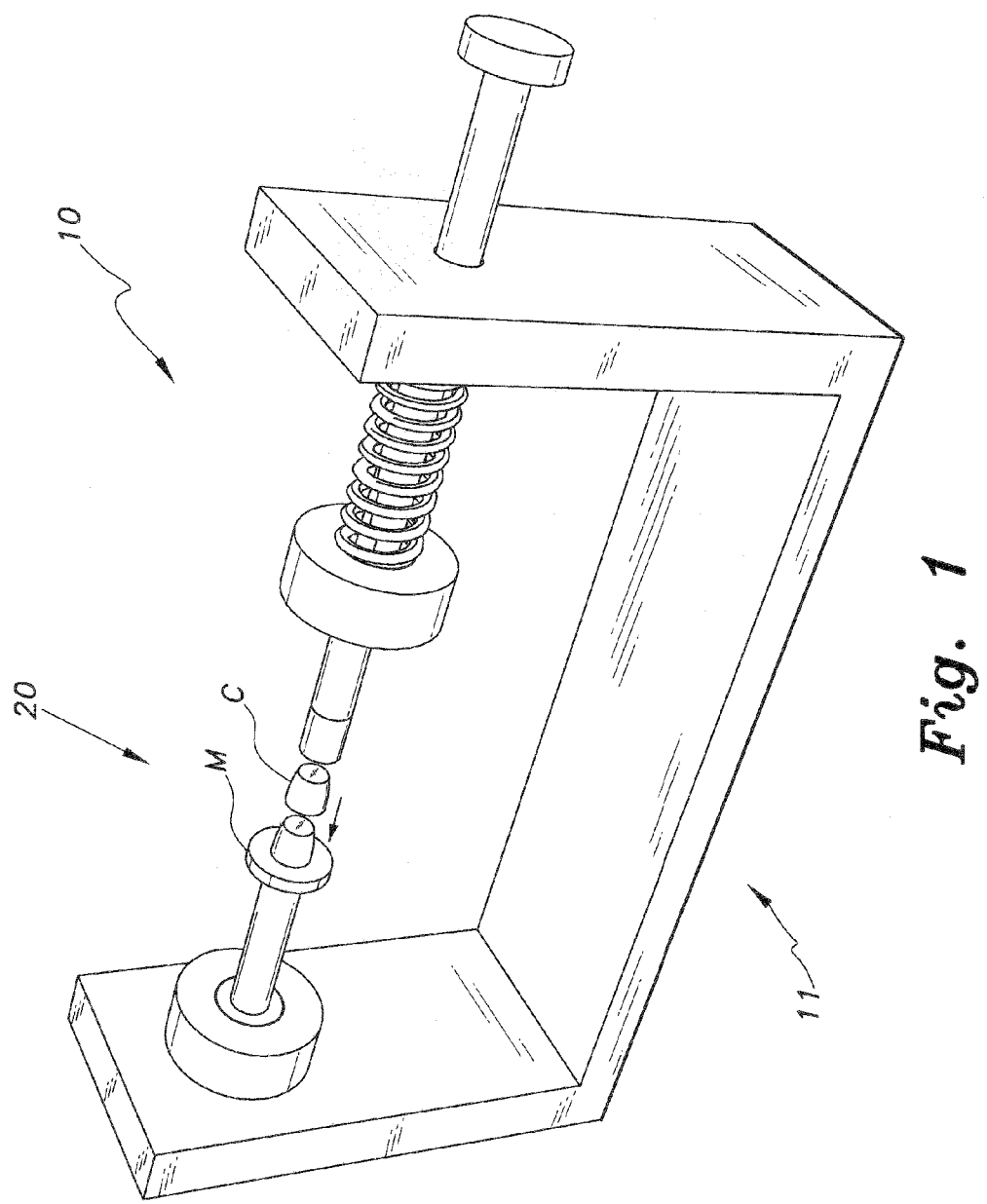
FIG. 1 is an environmental, perspective view of a stabilizing device for dental crowns according to the present invention, with a master model and a crown of a crown/tooth assembly broken away for clarity.
Figure 2:
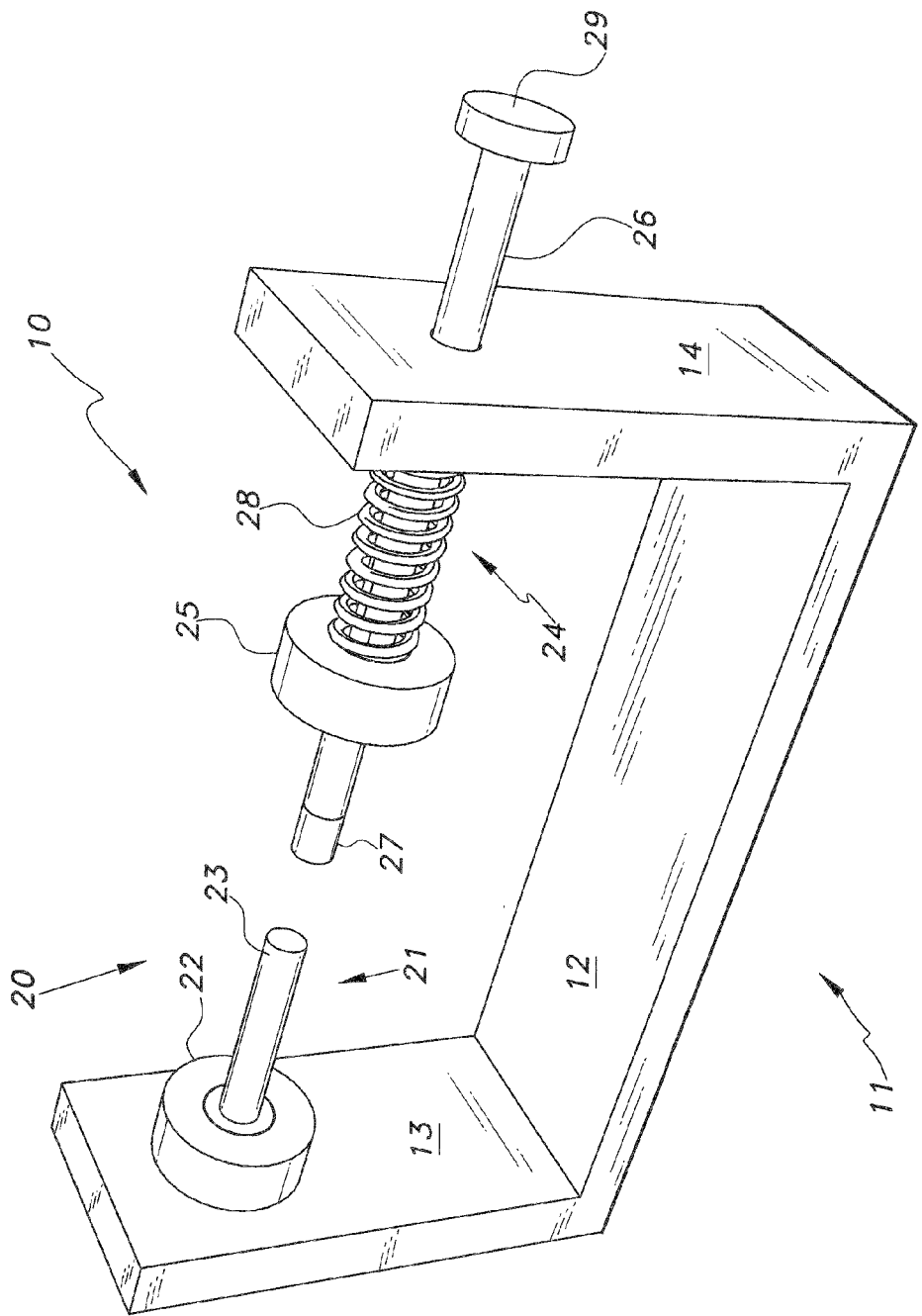
FIG. 2 is a perspective view of the stabilizing device for dental crowns shown in FIG. 1.

A stabilizing device for dental crowns, generally referred to by the reference number 10 in the Figures, is an adjustable holder for holding an assembled combination of a master model or prepared tooth structure and a dental crown, i.e., crown/tooth assembly, in a stable manner. The stabilizing device for dental crowns can rotatably support the crown/tooth assembly so that scans and measurements may be performed at various positions of the crown/tooth assembly for more accurate assessment of fit and/or crown configuration, especially the marginal gap. As best seen in FIGS. 1 and 2, the stabilizing device 10 includes a base 11 and a clamp assembly 20 rotatably mounted thereon.

The base 11 is a U-shaped frame including an elongate bottom member 12, an elongate first upright member 13 extending upwardly from one end, and an elongate second upright member 14 extending upwardly from the opposite end of the bottom member 12. Each upright member 13, 14 rotatably supports separate components of the clamp assembly 20.

Figure 3:
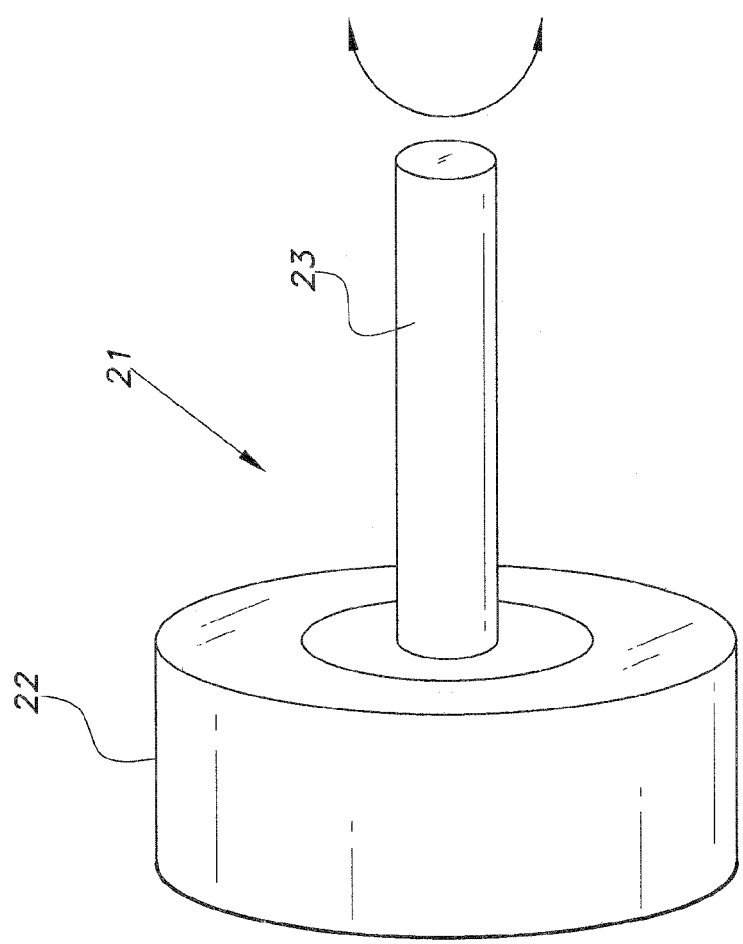
FIG. 3 is a perspective view of a rotating bearing assembly for the master model in the stabilizing device for dental crowns shown in FIG. 2.

The clamp assembly 20 includes a rotating spindle stock 21 mounted to the first upright member 13, and a rotating tail stock 24 mounted to the second upright member 14. As best seen in FIGS. 1-3, the spindle stock 21 includes a disk bearing 22 and an elongate holder shaft 23 extending coaxially through the disk bearing 22 and into the first upright member 13 when assembled. The holder shaft 23 is preferably free to rotate on the first upright member 13. Both the bearing 22 and the holder shaft 23 are preferably constructed from durable materials such as steel. Other high strength and durable materials such as plastic, composites, wood, and the like can also be used. In use, the distal end of the holder shaft 23 holds a master model M of a patient's tooth to be crowned.

Figure 4:
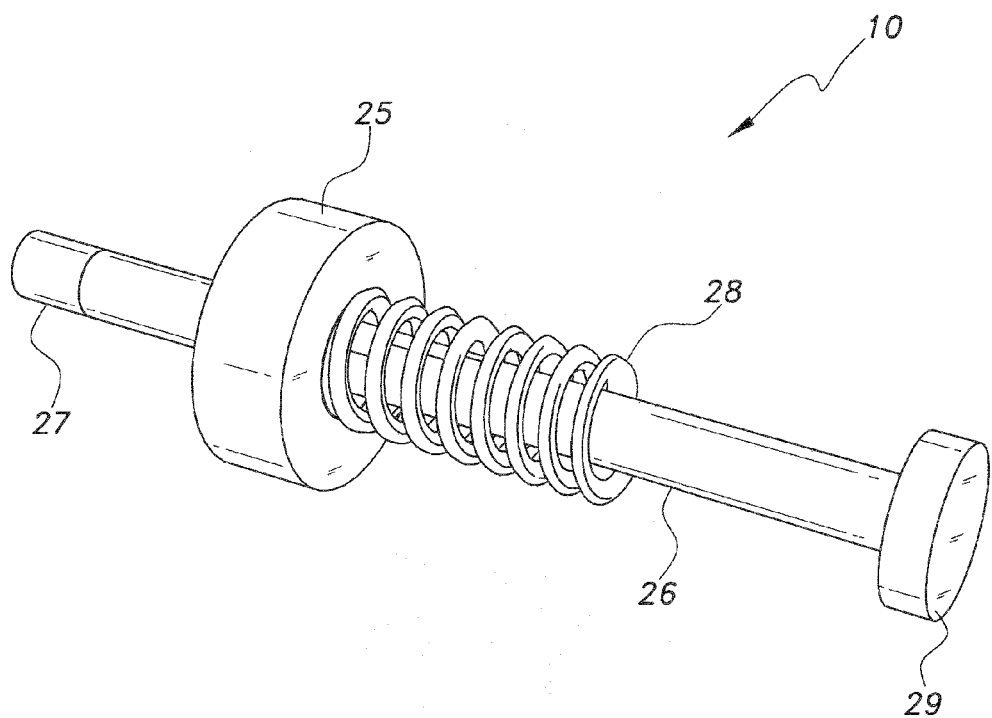
FIG. 4 is a perspective view of a rotating press assembly for pressing the crown against the master model in the stabilizing device for dental crowns shown in FIG. 2.

As best seen in FIGS. 1, 2, and 4, the tail stock 24 includes an elongate tail shaft 26 extending through a disk bearing 25 and through the second upright member 14 to enable the tail shaft 26 to rotate freely thereon. When assembled, the tail shaft 26 generally aligns coaxial with the holder shaft 23. One end of the tail shaft 26 is provided with a resilient holder tip 27, preferably constructed from silicone, rubber, or the like. In use, the holder tip 27 securely presses and holds a prepared crown C against the master model M. A handle 29 is provided at the opposite end of the tail shaft 26 for user manipulation. A user can manipulate the handle 29 to rotate the tail shaft 26 or move the tail shaft 26 towards or away from the holder shaft 23. The tail shaft 26 can be moved towards the holder shaft 23 to facilitate clamping of the crown C against the master model M. A biasing means, such as a spring 28, is slidably mounted around the tail shaft 26 so as to be disposed between the bearing 25 and the upright member 14. The spring 28 normally biases the holder tip 27 towards the distal end of the holder shaft 23.

In use, the user places the master model M at the end of the holder shaft 23 in preparation for clamping the crown C thereon. The master model M can be positioned on the holder shaft 23 by hand. The master model M can be further secured to the holder shaft 23 by providing mating threads, releasable latches, or a socket arrangement. To clamp the crown C onto the master model M, the user pulls the handle 29 outwardly to increase the gap between the distal end of the holder shaft 23 and the holder tip 27. The crown C is placed near or on the holder 27 and the handle 29 is released, which allows the spring 28 to return to the normally biased direction and gently clamp the crown C onto the master model M. The spring 28 preferably has a predetermined spring constant so that relatively consistent pressure can be applied to the clamped model/crown. Once clamped, the assembled model/crown M, C is ready to be scanned by a traveling microscope or the like. Additional scans and/or measurements can be performed by manually rotating the handle 29 to another position. Though the clamp assembly 20 is freely rotatable, the clamp assembly 20 can be configured so that the rotation is incremental or indexed at predetermined intervals. Either method permits numerous scans to be performed at different locations, which results in a more accurate assessment of the true marginal gap.

It is to be understood that the present invention is not limited to the embodiments described above, but encompasses any and all embodiments within the scope of the following claims.

I claim:

1. A stabilizing device for dental crowns, comprising:
    an elongate base;
    a pair of opposing upright members extending from the elongate base; and
    a rotating clamp assembly coupled to the upright members, the clamp assembly having a spindle stock rotatably supported on one of the upright members and a tail stock rotatably supported on the other upright member, the spindle stock adapted to support a master model thereon and the tail stock adapted to support a crown thereon, the clamp assembly configured to selectively and resiliently press the crown against the master model and stabilize the assembled crown/model for subsequent scanning;
    the spindle stock including:
    a bearing fixedly attached to the one of the upright members; and
    an elongate holder shaft extending coaxially from the bearing, the elongated holder shaft having a distal end adapted to support the master model thereon, and the elongated holder shaft being freely rotatable in the bearing.

2. The stabilizing device for dental crowns according to claim 1, wherein the tail stock comprises:
    an elongate tail shaft including a resilient tip attached to one end of the tail shaft, the resilient tip adapted to resiliently support the crown against the master model;
    a handle coupled to the opposite end of the tail shaft, the handle facilitating manual rotation of the clamp assembly;
    a bearing coupled to the tail shaft between the resilient tip and the handle; and
    a spring coupled to the tail shaft, the spring normally biasing the resilient tip towards the spindle stock, the spring providing clamping force for stabilizing and holding the assembled crown/model.

3. A system for measuring marginal gap comprising:
    a traveling microscope for measuring marginal gap; and
    a stabilizing device for dental crowns, the stabilizing device including
    an elongate base,
    a pair of opposing upright members extending from the elongate base, and
    a rotating clamp assembly coupled to the upright members, the clamp assembly having a spindle stock rotatably supported on one of the upright members and a tail stock rotatably supported to the other upright member, the spindle stock adapted to support a master model thereon and the tail stock adapted to support a crown thereon, the clamp assembly configured to selectively and resiliently press the crown against the master model and stabilize the assembled crown/model for subsequent scanning;
    the spindle stock including:
    a bearing fixedly attached to the one of the upright members; and
    an elongate holder shaft extending coaxially from the bearing, the elongated holder shaft having a distal end adapted to support the master model thereon, and the elongated holder shaft being freely rotatable in the bearing.

4. The system for measuring marginal gap according to claim 3, wherein the tail stock comprises:
    an elongate tail shaft including a resilient tip attached to one end of the tail shaft, the resilient tip adapted to resiliently support the crown against the master model;
    a handle coupled to the opposite end of the tail shaft, the handle facilitating manual rotation of the clamp assembly;
    a bearing coupled to the tail shaft between the resilient tip and the handle; and
    a spring coupled to the tail shaft, the spring normally biasing the resilient tip towards the spindle stock, the spring providing clamping force for stabilizing and holding the assembled crown/model.

* * * * *